United States Patent [19]

Haverl et al.

[11] 4,137,777
[45] Feb. 6, 1979

[54] ULTRASONIC BODY SCANNER AND METHOD

[75] Inventors: Ronald A. Haverl, Andover; Milton Stoller, West Hartford, both of Conn.

[73] Assignee: Mediscan Inc., South Windsor, Conn.

[21] Appl. No.: 814,477

[22] Filed: Jul. 11, 1977

[51] Int. Cl.² ............................................. G01N 29/04
[52] U.S. Cl. ........................................ 73/620; 73/626; 73/633; 73/642; 128/2 V
[58] Field of Search ...................... 73/612, 618–621, 73/625, 626, 641, 642, 644, 628; 340/1 R, 5 MP, 9; 128/2 V; 310/336, 366, 371

[56] References Cited

U.S. PATENT DOCUMENTS

| | | | |
|---|---|---|---|
| 2,593,865 | 4/1952 | Erdman | 73/622 X |
| 3,086,195 | 4/1963 | Halliday | 73/640 X |
| 3,166,731 | 1/1965 | Joy | 73/626 X |
| 3,918,024 | 11/1975 | Macovski | 73/626 X |
| 3,924,454 | 12/1975 | McElroy et al. | 73/642 X |
| 4,005,382 | 1/1977 | Beaver | 340/1 R |
| 4,012,952 | 3/1977 | Dory | 73/612 X |
| 4,034,332 | 7/1977 | Alais | 73/603 X |
| 4,058,003 | 11/1977 | Macovski | 73/620 X |

FOREIGN PATENT DOCUMENTS 184000  8/1966  U.S.S.R. ............................ 73/67.8 S

OTHER PUBLICATIONS

A. C. Eggleton, State-of-the-Art of Single-Transducer Ultrasonic Imaging Technology Medical Physics, vol. 3, No. 5, pp. 303–311, Oct. 1976.

*Primary Examiner*—S. Clement Swisher
*Assistant Examiner*—John P. Beauchamp

[57] ABSTRACT

Non-destructive testing with ultrasonic energy is performed by scanning a focused ultrasound beam until a region of interest is detected and rescanning this region with the beam focused at a plurality of depths. Apparatus for ultrasonic body scanning for medical purposes may include an actively driven transducer crystal which may be dynamically focused. A beam of energy produced by the transducer will be coupled to the patient by a liquid path and a movable mirror may be interposed along the liquid path to cause scanning of the beam.

36 Claims, 18 Drawing Figures

ULTRASONIC BODY SCANNER AND METHOD

BACKGROUND OF THE INVENTION (1) Field of the Invention

The present invention relates to non-destructive testing and particularly to the non-invasive examination of soft tissue and body organs. More specifically, this invention is directed to medical ultrasonic equipment and particularly to pulse-echo body scanners. Accordingly, the general objects of the present invention are to provide novel and improved methods and apparatus of such character.

(2) Description of the Prior Art

While not limited thereto in its utility, the present invention is particularly well suited for use in diagnostic medicine. Apparatus and techniques which permit the non-invasive examination of soft tissue organs are, for obvious reasons, of considerable interest. Presently available techniques for performing "imaging" of soft tissue organs include x-ray, nuclear medicine, thermography and, to a much lesser extent, diagnostic ultrasound. Nuclear medicine is, of course, an invasive technique, thermography has very limited utility and the degree of information which can be provided by conventional x-rays is limited; i.e., x-rays are not well suited for the imaging of soft tissues. Further, with imaging techniques other than diagnostic ultrasound, there may be some restriction to repeating the test if inconclusive results are obtained. In the case of nuclear medicine, for example, an inconclusive or unsatisfactory radioisotope scan may require the patient to be subjected to the reinjection of the radioisotope. As an additional disadvantage thereto, radioisotope scans and x-rays are notoriously expensive procedures.

Ultrasonic diagnostic techniques, because of the very high benefit to risk ratios for the patient and the ability to perform imaging of soft tissue organs that no other modality can provide, are attracting ever increasing interest. Thus, ultrasonic diagnosis has found applicability in obstetrics and gynecology, cardiology, neurology, ophthalmology and urology in addition to crossing over medical disciplines with the imaging of various internal body organs. In some situations invasive techniques for studying the heart, such as cardiac catheterization and angiography, can be replaced by ultrasonic techniques. Similarly, ultrasonic diagnosis has found use in the diagnosis of mitral stenosis. The widespread utility notwithstanding, the adoption of this modality has been impeded by inherent limitations in the equipment previously available.

Ultrasonic diagnostic instruments operate on either a pulse-echo or Doppler principle. The pulse-echo principle, which is primarily used for the imaging of soft body tissue, involves the transmitting of short bursts of ultrasonic energy and recording echoes reflected from anatomic structures within the body. Since the time required for an emitted pulse to return as an echo indicates the distance of the target structure from the transducer, the "echo gram" provides both a picture of the object and a graphic recording of any changes in the objects position. Thus, ultrasonic diagnosis is based on the reflection of ultrasonic waves which occur at the boundaries between different tissues within the body. A fraction of the incident energy is reflected if there is a change in characteristic impedance at such a boundary; impedance being defined as the product of the density of the tissue multiplied by the velocity of sound. Although the echoes which correspond to soft tissue boundaries have very small amplitudes, these echoes can be detected by a receiver having the requisite sensitivity. Energy which is not reflected travels beyond the boundary, and may be reflected at deeper boundaries. The maximum penetration is limited by the attenuation of the ultrasonic wave in passing through the tissues; attenuation being defined as the decrease in intensity of the sound pulse per unit of distance as it propagates in the medium and loses energy as the result of absorption and scattering.

Ultrasonic diagnostic instruments employ a transducer which converts electrical signals into acoustic pulses which are coupled into the tissue of the patient. The transducer may also serve the dual function of receiver for detecting the reflected pulses from within the patient. The transducers employed in ultrasonic body scanners are typically piezoelectric elements comprised of ceramic materials such as synthetic lead zirconate titanate. An ultrasonic diagnostic instrument will also comprise an oscillator which establishes the pulse repetition frequency and a linear power amplifier which excites the transducer through a coupling circuit. A decoupler permits the transducer to be used as both a transmitter and a receiver. The received pulses; i.e., the echoes returned from within the patient's body; are converted into electrical signals in the manner known in the art, these electrical signals are processed and the processed signals are presented on a display. The display will typically be a cathode ray tube and the oscillator which controls the transducer may also be employed to generate a time base trace for the display.

In order to obtain maximum utility from the instrument, two-dimensional images of various organs or body regions of interest must be generated. This can be accomplished by "scanning" wherein the transducer is moved back and forth. In the prior art the most common method of scanning involves contact scanning in which the transducer is placed directly on the patient's skin and moved, through a type of compound scan, in stepwise fashion. The information obtained must be optimized through coordinated movement of the transducer to achieve a meaningful image. Accordingly, a high degree of skillful operator interaction with the instrument is essential for a successful ultrasonic examination employing prior art equipment and it has been exceedingly difficult to duplicate initial test results since repeatability was almost totally dependent upon operator placement of the transducer.

The high degree of operator skill required and the extreme difficulty in repeating test results have, in part, been a consequence of the use of small size contact transducers; this small size resulting from the necessity of fitting the transducer to the contour of the skin. Prior art ultrasonic body scanners, as a consequence of their use of small contact transducers, were also characterized by slowness of use since the ability to find the area of interest was limited to trial and error scans. It is to be noted that the small size of the transducers, the slowness of the procedure and the difficulty in obtaining repeatability was also attributable to the fact that the prior transducers and associated apparatus lacked both the ability to electronically focus the "beam" of ultrasonic energy over the entire examination depth of interest and the ability to easily aim the "beam".

Prior ultrasonic diagnostic equipment has also been characterized by insufficient resolution over the desired examination range in the body; this examination range or field of examination typically being on the order of 20 centimeters. In order to be practical, an ultrasonic diagnostic device must have the ability of providing real time images of high resolution. The required characteristics, which result only from minimizing beam width and side lobes, have been lacking in the prior art. A further deficiency of prior art ultrasonic body scanners has resided in their poor dynamic range. The returns or echoes from the signal propagated into the body may vary over a range of 100 db. It is impossible to record the $10^6$ shades of gray which correspond to a 100 db range. It is, accordingly, prior practice to compress the signals generated by echoes through either the use of logarithmic amplifiers or by simple time gain compensation circuits. Using the prior art compression techniques, however, important information contained in the received signals has been lost.

With particular respect to the transducers employed in the prior art, briefly noted above the transducers previously used have not been capable of being focused electronically to achieve variable examination depth. Prior art transducers have typically been of a flat contour; i.e., have had no natural focus; and accordingly have been characterized by large magnitude side lobes which give spurious signals from off-axis targets and also result in ambiguity in range measurements because of the different path lengths for the echoes from the same object.

SUMMARY OF THE INVENTION

The present invention overcomes the above briefly discussed and other deficiencies and disadvantages of the prior art and in so doing provides "echo grams" which are real time images of high resolution. The apparatus which permits the achievement of such high quality images is characterized by the ability to dynamically focus the beam of ultrasonic energy and to scan the beam in multiple planes with a single placement of the ultrasound transducer relative to a body to be examined. Dynamic focusing and multiple plane scanning, in turn, provide repeatability of results since the results of an examination are not totally dependent on operator placement of the transducer.

In a preferred embodiment, a generated beam of ultrasonic energy will be focused at a preselected depth and will be scanned at a first rate along a line or plurality of "parallel" lines. When an area of interest is observed, the beam will be caused to rescan such area while its focal length is varied.

Also in accordance with a preferred embodiment, the ultrasonic energy is coupled to the patient via a liquid path. Scanning of the beam is accomplished by inserting a steerable acoustical mirror in the liquid path.

Apparatus in accordance with the invention may also employ a transducer having a natural focal length; i.e., a shaped piezoelectric crystal; which is actively driven. The crystal, in accordance with one embodiment, has a plurality of coaxial annular electrodes which are individually driven.

BRIEF DESCRIPTION OF THE DRAWINGS

The present invention may be better understood and its numerous objects and advantages will become apparent to those skilled in the art by reference to the accompanying drawing wherein like reference numerals refer to like elements in the various figures and in which.

DESCRIPTION OF THE PREFERRED EMBODIMENT

Figure 1:
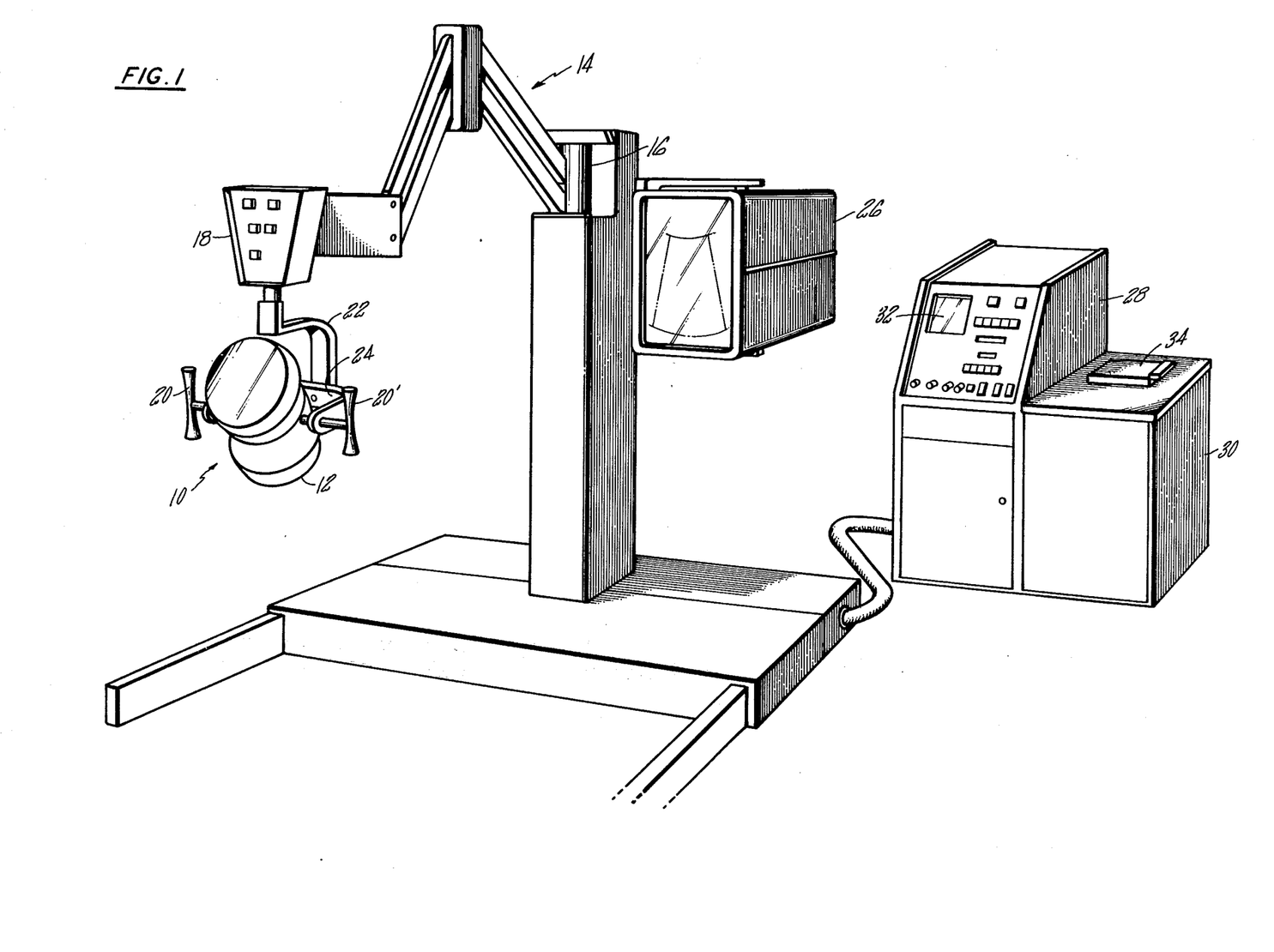
FIG. 1 is a perspective view of a first embodiment of an ultrasonic body scanner in accordance with the present invention.

With reference now to FIG. 1, an ultrasonic body scanner in accordance with a first embodiment of the present invention is shown. The body scanner includes a head assembly, indicated generally at 10, which houses a transducer and means for controlling the scanning of the beam generated by the transducer. The present invention employs a transducer which preferably has a comparatively large area. Also, the transducers employed in the present invention are preferably also characterized by having a natural focal length. Since a large area transducer will not normally conform to the contour of the patient's body, flexible means must be provided to couple the ultrasonic energy from the transducer into the patient. In the disclosed embodiment the coupling means comprises a flexible bladder 12 filled with a liquid such as water and/or other liquid with low sound absorption qualities. As will be seen from FIG. 5, the front face of the actual transducer element is immersed in the fluid within bladder 12. This offers the important advantage of permitting high speed sector scanning without repositioning the head with respect to the patient. Also, separation of the transducer from the body permits focusing of the beam of ultrasonic energy close to the patient's skin line.

Head 10 is supported on the free end of an articulated arm which has been indicated generally at 14. The construction of arm 14 is such that head 10 may be raised, lowered, moved toward or away from the support column 16 for arm 14 and pivoted about the axis of the support column 16. Thus, head 10 has six degrees of freedom of motion whereby any plane in the body can be visualized and objects such as veins can be tracked as they course through the body. Head 10 is mounted from arm 14 via a pair of yokes 22, 24 which permit a limited degree of movement of the head with respect to the arm so as to permit optimizing the contact between bladder 12 and the patient. A control panel 18 is also mounted on arm 14 immediately above head 10. Through use of controls on panel 18 the operator may select the scanning mode of the transducer within head 10 and particularly the rate, area and depth of the scan. The operator may also, via control panel 18, control the taking of photographs of regions of interest. The movements of head 10 are physically controlled by the operator; i.e., the position of the scanning head on the patient is manually changed by steering the head through use of a pair of handles 20, 20'.

A monitor 26, which may be a conventional television receiver, is mounted from the support column for the arm mechanism 14 as shown. The monitor 26 is positioned so as to provide the operator with a visual presentation of the area being scanned whereby the operator will be assured that the head is properly positioned and will be given information which will enable him to change scanning modes, for example from a fast to a slow scan, and to activate the camera.

The power supplies and control circuitry necessary for operation of the body scanner, as well as the circuitry for processing received signals, are mounted in a pair of equipment cabinets 28 and 30. Cabinet 30 includes, in addition to a main control panel, an "A" scan scope which is typically a cathode ray tube. Scan scope 32 displays the raw signal produced by the transducer in head 10 in response to the receipt of echoes; i.e., the scope 32 displays echo amplitude versus time (depth). The "A" scan provides information to the operator which is initially employed for adjusting the gain controls of the apparatus so as to achieve equal amplitude for signals commensuate with echoes received over the entire range of depth of examination. The "A" scan also provides information, not easily ascertainable from photographs, as to the magnitude of the received echoes. This information may be of interest in interpreting the results of an examination. In response to the information provided on scope 32, typically at the beginning of an examination, the operator will adjust a time gain control which is actually a curve shaping control. Equipment cabinet 30 includes a further cathode ray tube and a TV camera tube which are employed to produce and transmit a two-dimensional image back to the TV monitor 26. The signal displayed on the cathode ray tube in cabinet 30 will be the raw signal from the transducer processed so as to give a two-dimensional body scan. A camera 34 is mounted on cabinet 30 so as to permit the making of a permanent record of the results of the scan; camera 34 taking a picture of the display on the cathode ray tube and being controlled from panel 18 as discussed above.

Figure 2A:
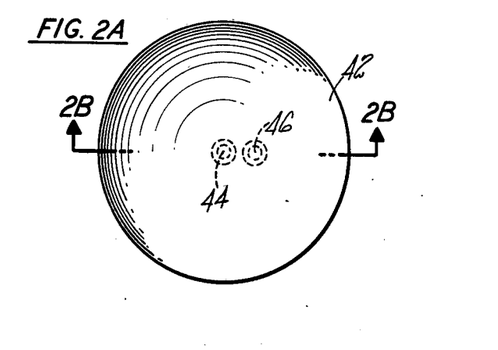
FIGS. 2A and 2B are respectively front plan and cross-sectional side elevation views of a first embodiment of a transducer crystal which may be employed in the apparatus of FIG. 1.
Figure 2B:
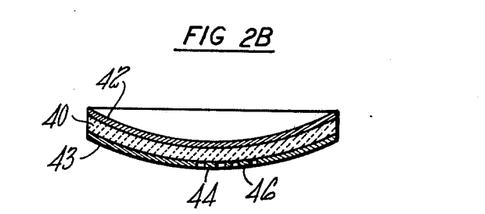
Figure 3:
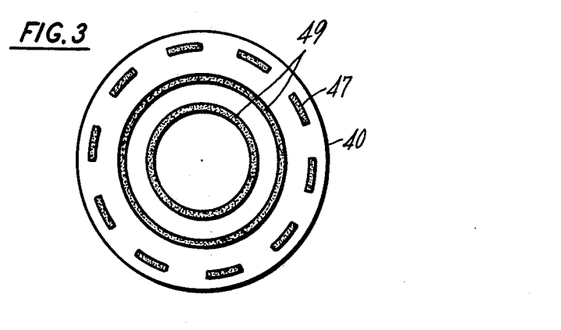
FIG. 3 is a rear plan view of a second embodiment of a transducer crystal which may be employed in the apparatus of FIG. 1.

Referring now to FIGS. 2–4, various transducers which may be employed in the practice of the present invention are depicted. The transducers are fabricated from a wafer or disc of piezoelectric material, typically a ceramic such as lead zirconate titanate, and preferably have the common characteristic of a concave front or emitting surface and a convex rear surface as may be seen from FIG. 2B. The transducer could, however, be a flat crystal having a concave acoustical lens bonded to the front surface thereof. In such case the lens would typically be fabricated from a plastic including a suitable filler which gives the desired propagation velocity. The lens material should also have an absorption coefficient of zero, an impedance which is matched to that of the crystal and a refractive index which is not unity. Thus, the transducers employed in the preferred embodiment of the invention have a natural focus which will typically be 30 centimeters from the center of the transducer. In order to permit energization of the transducers by the application of an electrical signal, to thereby generate a sound pulse, all or portions of the opposed faces of the ceramic wafer must be coated with electrically conductive material. The presence of such electrodes on the transducer also permits the sensing of electrical signals generated by the piezoelectric material in response to pressures applied to the material commensurate with received echoes.

FIG. 2 depicts a transducer electrode configuration particularly well suited for the imaging of tumors. In the FIG. 2 embodiment the entire front surface of the tuned piezoelectric wafer 40 is coated with a layer of conductive material 42 as may be seen from FIG. 2B. As best seen from FIG. 2A, the opposite or back surface of wafer 40 is, with the exception of a pair of annular regions, also completely coated with the electrode material as indicated at 43. These two annular regions define, in their centers, a pair of discrete electrodes 44 and 46. Electrode 44 is disposed on the axis of the transducer while electrode 46 is displaced from the axis. The discrete electrodes 44 and 46 are employed only in the receiving mode.

FIG. 3 depicts, in a plan view, an electrode configuration which may be employed for both the front and back surfaces of the shaped piezoelectric wafer. The electrode of FIG. 3 is characterized, extending outwardly from the axis thereof, by a plurality of concentric rings 49 of electrode material; the circles of conductive material being aligned on the opposed faces of the transducer. Use of a plurality of concentric circles of electrode material on at least the back surface of the piezoelectric wafer permits the electronic focusing of the transducer whereby the examination depth may be varied about the natural focal length of the transducer. Also in accordance with the FIG. 3 embodiment, the outer electrode ring 47 is segmented. The segmented electrode is employed for receiving purposes only. It has been found that, to obtain optimum results, the width of ring 47 should be less than ten wavelengths of the transmitted ultrasonic energy and should preferably be about three wavelengths.

As an alternative to the electrode arrangement depicted in FIG. 3, it is possible to employ an annular lead zirconate titanate crystal, having a width which corresponds to one-half the wavelength of the transmitted ultrasonic signal, on which the segmented electrodes are deposited. A separate transmitting transducer would, in this case, be mounted on the axis of such an annular transducer.

Figure 4A:
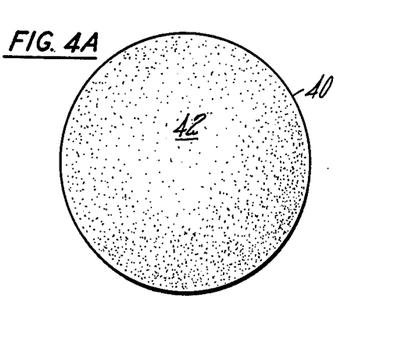
FIGS. 4A and 4B are respectively front and rear plan views of a further embodiment of a transducer crystal which may be employed in the apparatus of FIG. 1.
Figure 4B:
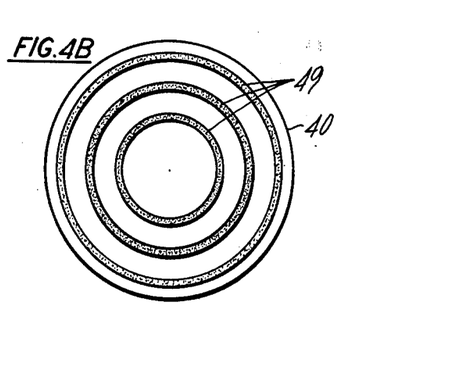

Considering FIG. 4, a further embodiment of a transducer for use in accordance with the present invention is depicted. In the FIG. 4 embodiment, as shown in FIG. 4A, the entire front surface of the tuned or focused piezoelectric wafer is covered with electrode material. The rear surface of the transducer, as may be seen from FIG. 4B, is identical to the electrode configuration of FIG. 3 with the exception that the segmented outer electrode is omitted. The focal length of the transducer of FIG. 4 may be varied electronically about the natural focal length.

The discrete electrodes of the FIG. 2 embodiment may be incorporated into any of the other disclosed transducer embodiments.

To discuss further the above described transducer configurations, in pulsed ultrasonic body scanning, and particularly in B-mode scanning wherein the object is to intensify reflection points on a cathode ray tube, a short burst of ultrasonic energy will be transmitted by the piezoelectric transducer into the body in the form of a narrow beam. As this beam progresses into the body it encounters tissue substances and interfaces between tissue structures which scatter back some of the incident energy. The returning signals or echoes are converted back into electrical signals by a receiver transducer which may be the same element as the transmitting transducer. The nature of the echoes scattered back in the direction of the receiver transducer is extremely varied and depends upon the nature of the tissues responsible for the scattering. A tissue structure which is small compared to the wavelength of the insonifying energy will scatter energy equally in all directions; i.e., there will be diffuse reflectances. Tissue structure which is large and flat, however, will function as a mirror and reflect the incident energy in one direction; i.e., specular reflectances will result. Generally, body tissue will exhibit a combination of diffuse and specular reflectance patterns. It has long been desired in the art to enhance the diffuse reflectances relative to the specular reflectances. Such enhancement of the diffuse reflectances will produce an improved image as the specular echoes tend to be one or two orders of magnitude larger than the diffuse reflectances. Enhancement of diffuse reflectances has not previously been successfully accomplished in ultrasonic scanners intended for medical purposes partly because the large specular echoes overpower and obliterate the weaker diffused echoes in both the penetration depth; i.e., range; and asmuth directions. This obliteration, in part, is a result of the presence of side lobes in the transmitted signal and thus in the echoes; side lobes being inherently present in a diffraction limited energy beam and resulting from fringing effects. Thus, ultrasound directivity patterns not only have a central main lobe, through which most of the energy returns, but also include side lobes through which off-axis signals may enter. If the main lobe is directed towards a weak echo, a stronger off-axis signal such as a specular echo may enter the side lobes and completely obliterate the small signal that is on-axis. It is also to be noted that very large echoes can saturate the amplifiers coupled to the receiver transducer thereby resulting in the "blooming" of the display on the cathod ray tube with the resultant obliteration of small signals.

In accordance with one embodiment of the present invention the diffuse reflectance may be enhanced through the use of a separate receiver in the form of a segmented annulus. As discussed in the description of FIG. 3, the electrode annulus representing the receiver may be divided into several elements by segmenting an outer electrode ring on both sides of the transducer into corresponding sections. The electrodes are connected cyclically; i.e., a "first" rear electrode is connected to a "second" front electrode, the "second" rear electrode is connected to a "third" front electrode, etc. The electrodes are thus electrically interconnected in a series aiding configuration. When reflected energy is received equally by all regions of the annulus, characteristic of a diffuse reflectance, voltages which add together are generated. A specular echo, if it strikes the annulus at all, will strike only one or two regions where segments of the receiver ring are present. Thus, by way of example, if there are ten elements in the receiver, a diffuse echo would generate a voltage ten times higher than an equal magnitude specular echo impinging on a single segment.

It is to be understood that, rather than connecting all of the elements in series, each pair of front and rear electrodes may be coupled to a separate amplifier and the amplified signals processed as desired. By way of example, the amplified signals from all of the electrodes could be averaged to produce a result which would be the same as a series aiding configuration. Also, if more complex signal processing is desired, signals commensurate with all of the echoes being of approximately the same magnitude could be accepted for display while the display would be inhibited if there was a wide discrepancy in the amplitude of the signals received at the segments around the annulus.

In accordance with another embodiment, which has achieved exceptionally good results, all of the electrode rings of either of the transducers of FIGS. 3 and 4 may be used as both transducing and receiving elements. The use of all electrode rings for focusing in a transducing mode and for receiving is particularly advantageous when employing the transducer configuration of FIG. 4.

Figure 5:
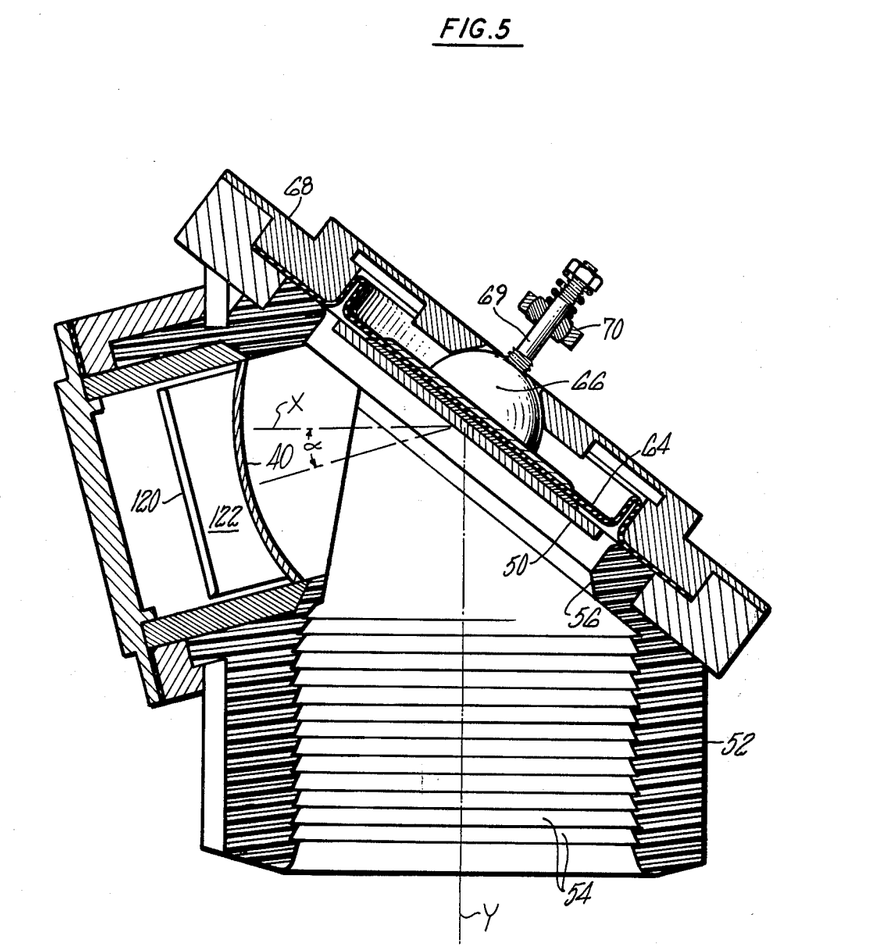
FIG. 5 is a cross-sectional side elevation view of the transducer head of the apparatus of FIG. 1.
Figure 6:
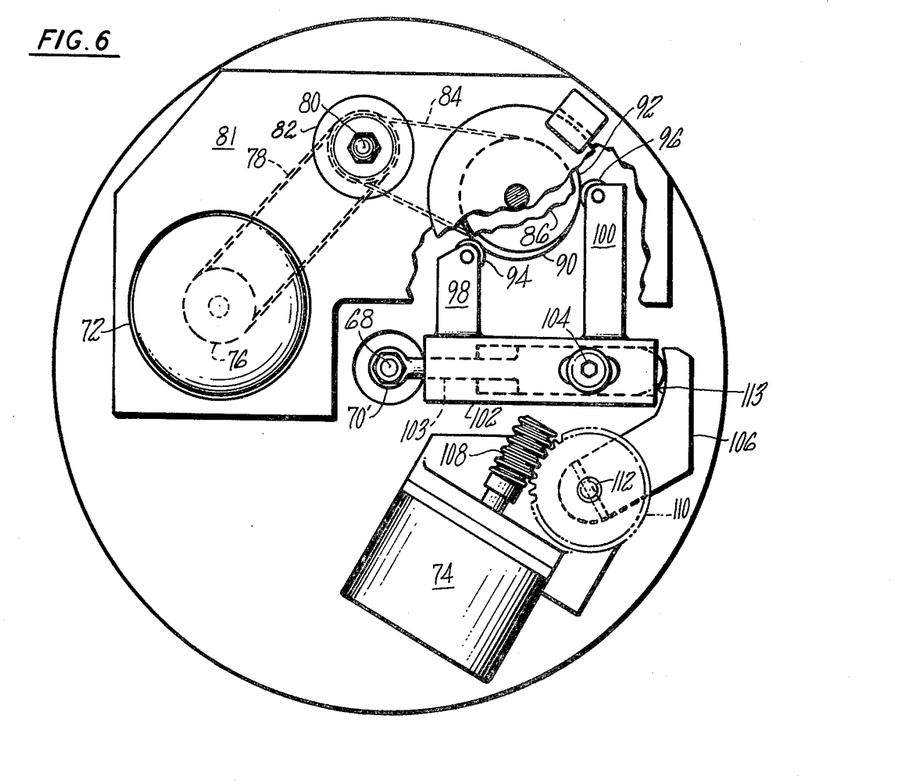
FIGS. 6 and 7 are respectively top and side elevation views of the beam scanning control mechanism of the apparatus of FIG. 1.

Referring now to FIG. 5, the transducer portion of the head 10 of the ultrasonic body scanner depicted in FIG. 1 is shown in cross-section. The principal elements of the transducer subassembly are the sonic generator and a scanning mirror. The sonic generator includes a focused piezoelectric crystal 40 while the mirror has been indicated at 50. Both the sonic generator and mirror are mounted within a housing 52 which is preferably molded from an elastomer or other plastic having suitable sound absorption characteristics. The lower end of housing 52, as the apparatus is shown in FIG. 6, will be mated to the bladder 12 which is brought into contact with the patient. Housing 52 will be filled with a suitable sound transmitting liquid and the front or transmitting face of crystal 40 and the face of mirror 50 will be immersed in this liquid. The "tubular" lower portion of housing 52, through which the ultrasonic beam is transmitted and via which the echoes are received, is provided with ribs 54 as shown. The purpose of ribs 54 is to dissipate any stray reflections; particularly from side lobes in the signal propagated from the crystal 40. The "annulus" 56, which defines the entrance opening to the cavity in housing 52 in which the scannable mirror 50 is positioned, will also serve to dissipate stray reflections and attenuate any reflectance from the edge of mirror 50.

Mirror 50, when in its median position, is offset with respect to the axis of the tubular lower portion or entrance aperture of housing 52 to further exclude stray body reflections which may result from distortions of the bladder 12. The optimum offset; i.e., the angle $\alpha$ between a line X originating at the point of intersection of the axis Y of the sound transmitting passage in housing 52 with the surface of mirror 50, and perpendicular to the surface of mirror 50, and the axis of the beam of ultrasound energy generated by crystal 40; has been found to be optimally 15°. The center of mirror 52 will always be intersected by a line through the center of transducer 40.

The sonic generator includes, in addition to crystal 40, a holder 120 into which the crystal is fitted. Holder 41 is filled with a material 122 which will absorb energy radiated from the rear surface of the crystal. Holder 120 also supports the conductors which are connected to the electrodes on the crystal and suitable isolation, summing and preamplifier circuitry. An individual "pulse" generator, which will be a low impedance source of electrical energy, will customarily be connected directly to each transducing electrode ring. Considering the transducer of FIG. 4, all of the electrode rings will also be connected to a summing circuit which, in turn, is coupled to a preamplifier.

In the disclosed embodiment mirror 50 comprises a flat surfaced stainless steel disc. The mirror is secured, by means of a suitable adhesive, to a diaphragm 64. The diaphragm 64 is secured as shown so as to function as a seal which renders housing 52 hermetic. The back surface of mirror 50 is rigidly attached, by any suitable means, to a hemispheric shaped member 66 which functions as a ball joint; the aforementioned line through the center of transducer 40 intersecting the center of the ball joint. Ball member 66 cooperates with bearing surfaces formed on a support table 68; diaphragm 64 being clamped between table 68 and housing 52. Ball member 66 is provided with a socket which receives an actuating rod 69. Rod 69 is driven so as to cause the scanning of mirror 50. The movements of actuator rod 68 are controlled, in the manner to be described below in the discussion of FIGS. 6 and 7, by drive mechanism which is partly shown at 70.

Figure 7:
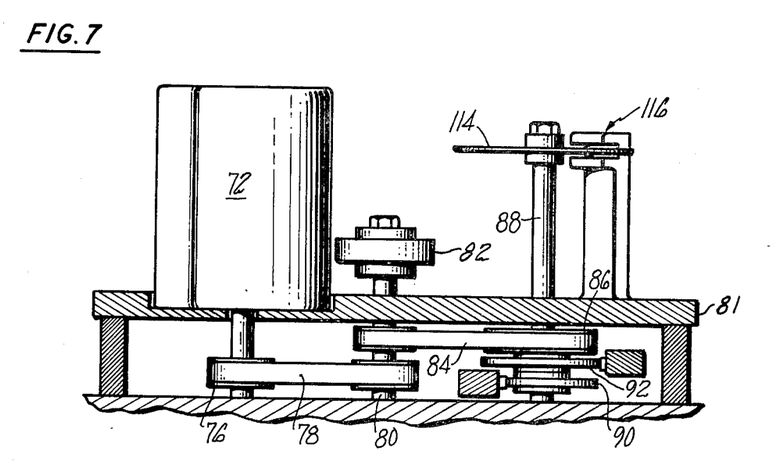

Referring now to FIGS. 6 and 7, the drive for mirror 50 comprises a first or primary motor 72, which is preferably a stepping motor, and a second tilt control motor 74, which may also be a stepping motor. Motor 72 drives a pulley 86 via a drive system including pulley 76, belts 78 and 84 and an idler shaft 80. A pair of idler pulleys are mounted on shaft 80 below a support plate 81 and a flywheel 82 is mounted on shaft 80 above plate 81. Pulley 86 is keyed to a rotatable shaft 88 on which are mounted a pair of conjugate cams 90 and 92. A pair of cams, which are the direct opposites of one another, are employed in the interest of avoiding the use of a spring to hold the cam followers against the cams. The use of conjugate cams 90 and 92 thus minimizes the size of drive motor 72; this being particularly true at high speeds when the followers tend to lift off the cams.

The cam-cam follower relationship may be clearly seen from FIG. 6. The cam followers 94 and 96 are respectively mounted at first ends of arms 98 and 100 and cooperate with respective cams 92 and 90. The second ends of arms 98 and 100 are affixed to a transversely oriented actuator arm 102. Arm 102 supports, by means of spaced bearings, a further actuator arm 103 (shown partially in phantom). Arm 103 follows any transverse movements of arm 102 but is capable of longitudinal movement relative to arm 102. Operation of primary scan motor 72 causes rotation of cams 90 and 92 with a rocking motion of actuator arm 102 resulting; the arm 102 pivoting about a pivot shaft 104. This oscillatory motion of arm 102 is transmitted to mirror drive shaft 68 by connector 70' formed on the end of arm 103. Thus, operation of primary drive motor 72 results in the mirror 50 being scanned back and forth (up and down as the apparatus is shown in FIG. 6) so that each point on the mirror will transcribe a line having a slightly arcuate shape. This, in turn, will cause the focal point of the ultrasonic beam to transcribe a line located at a depth in the patient; i.e., a distance from crystal 40; determined either by the natural focal length of crystal 40 or some other distance as selected through the electronic focusing of the transducer.

In order to shift the scan line to the left or right as the apparatus is depicted in FIG. 6, the position of a parallel plane cam 106 will be moved under the control of stepping motor 74; motor 74 driving cam 106 via a worm gear 108 and gear 110 whereby cam 106 will pivot about shaft 112. The end of arm 103 disposed oppositely to connector 70' is provided with a bearing surface 113 which rides on cam 106 as arm 103 follows the scanning motion of arm 102. Each time cam 106 is repositioned, the scan line will be stepped to a new position by tilting the mirror 50 in a direction generally transverse to the scan line as determined by the motion of arm 102 resulting from rotation of cams 90 and 92.

Referring again to FIG. 7, slotted disc 114 is mounted on and rotates with shaft 88. A photoelectric sensor, indicated generally at 116 and including a light source and light responsive detector element, is mounted so as to sense the passage of the slot or slots in disc 114. The signals generated by detector 116 are used to synchronize the display to the position of mirror 50.

Referring now to FIG. 8, a circuit block diagram of a control system for a preferred embodiment of the present invention is shown. The control system of FIG. 8 is intended for operation with a transducer of the type depicted in FIG. 4 wherein the front surface of the crystal is completely covered with electrically conductive material and the rear surface of the crystal has electrodes disposed thereon in the form of a plurality of concentric rings; the control of FIG. 8 specifically being applicable to a transducer with eleven such electrode rings. A highly schematic cross-sectional view of the electrode appears in FIG. 9 while FIG. 10 is a wave form diagram showing voltages which appear at various points within the control circuit of FIG. 8.

Continuing to refer to FIG. 8, the control system includes circuitry for "firing" the electrode rings on the transducer crystal in the proper sequence so as to achieve the desired depth of focus of the transmitted ultrasonic "beam". The control circuitry of the disclosed embodiment has the capability of selecting six zones or depths of focus with focal length Z3 being the natural focus of the shaped transducer crystal. When all eleven electrode rings are simultaneously energized, the resulting beam of ultrasonic energy will be focused at the natural focal length Z3 of the transducer. The control circuitry of the preferred embodiment of the invention also includes means for selecting different modes of operation, means for controlling the scanning of the ultrasonic beam as described above and means for processing and displaying and/or recording received echoes.

Figure 8A:
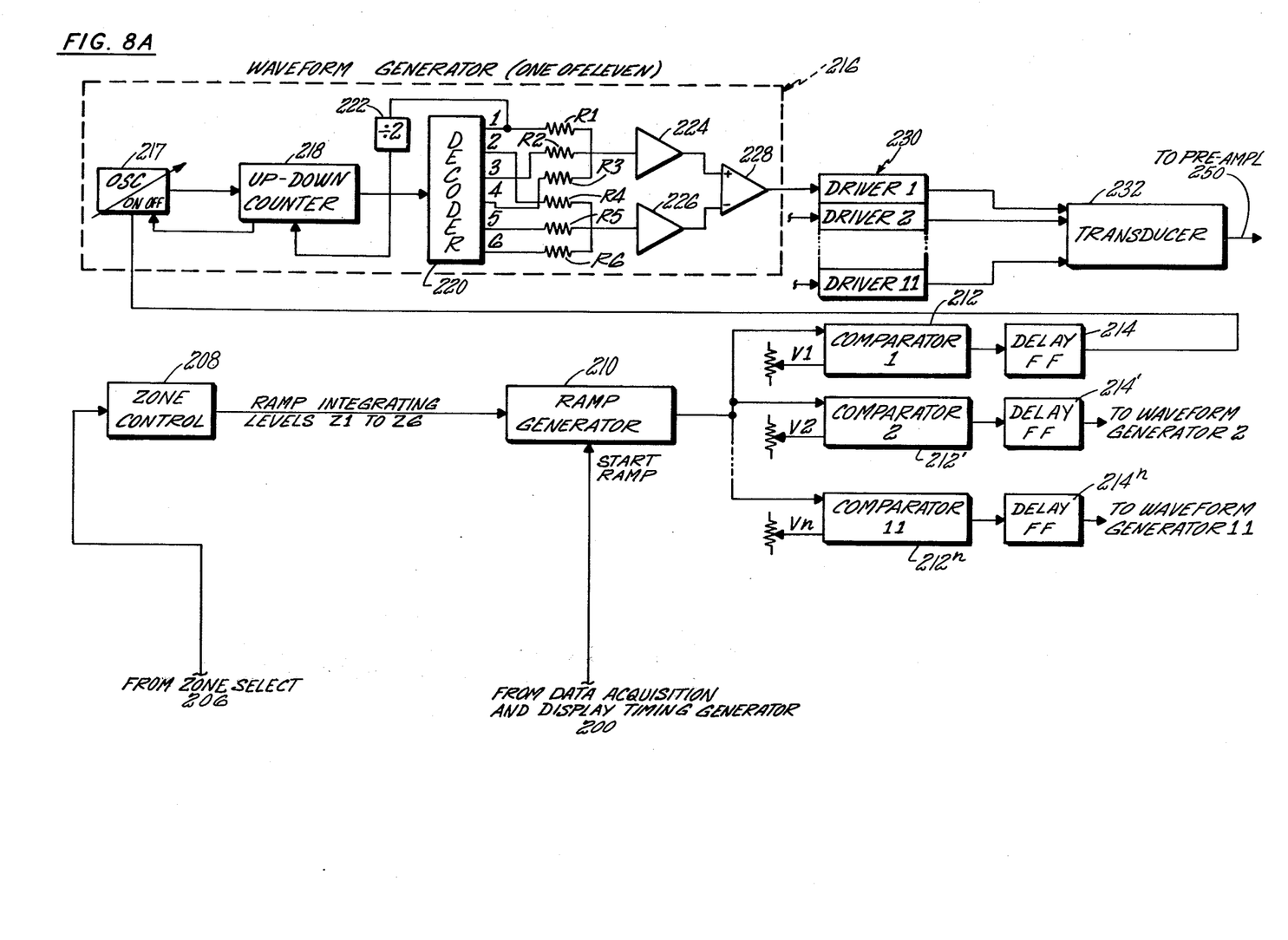
FIGS. 8A-8C inclusive comprise a functional block diagram of an electrical control circuit for the apparatus of FIG. 1.
Figure 8B:
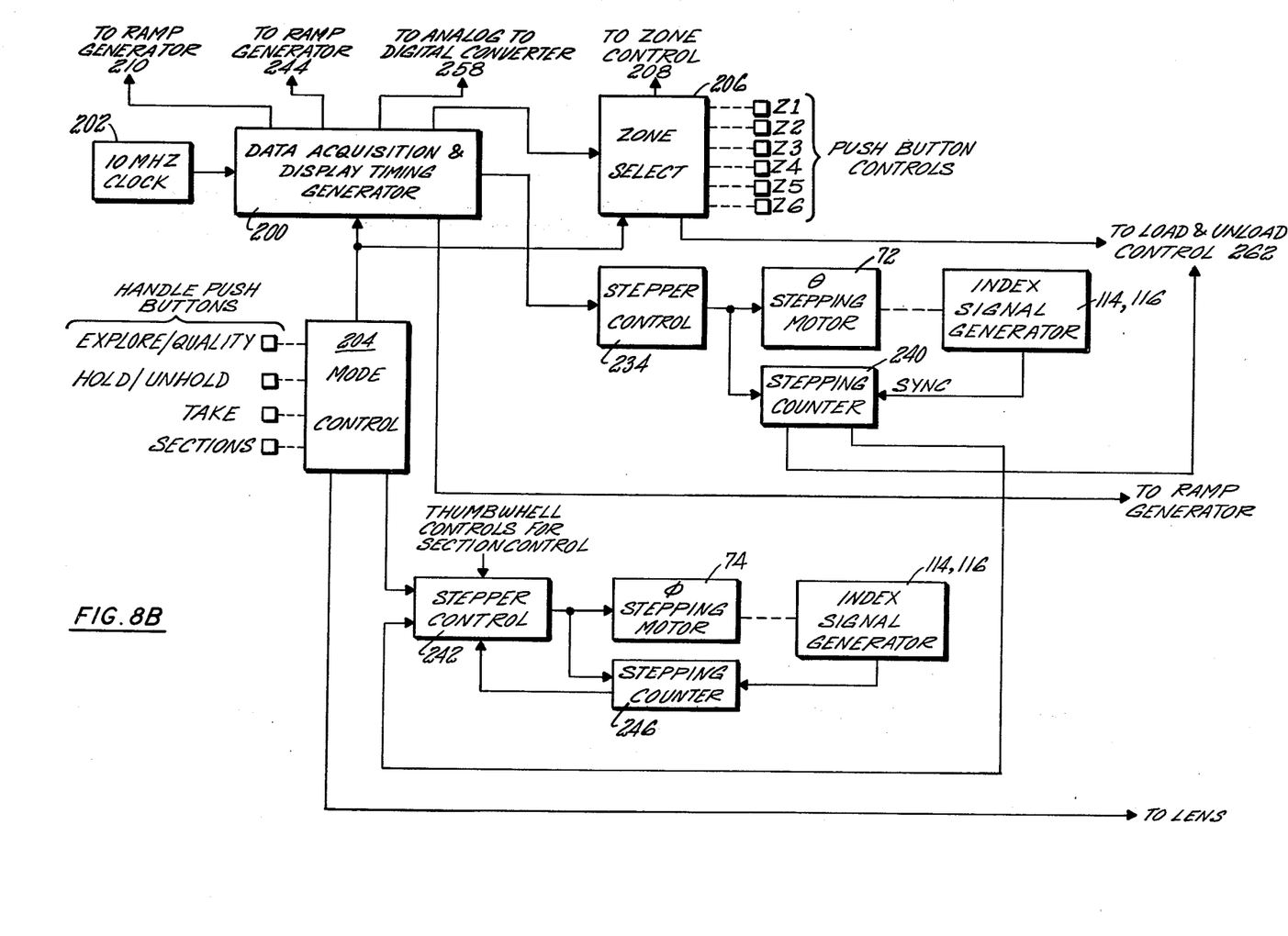

The various subsystems of the control circuitry of FIG. 8 are responsive to the outputs of a data acquisition and display timing generator 200 (FIG. 8B). Timing generator 200 receives, as input signals, the output of a clock pulse generator 202 and a output from a mode control selector circuit 204. Timing generator 200 divides down the output of clock 202 to provide, in the proper sequence, timing pulses which control the operation of ramp voltage generators 210 (FIG. 8A), 244 (FIG. 8C) and 272 (FIG. 8D) and controls the sampling rate of an analog-to-digital converter 258 (FIG. 8C). Timing generator 200 also produces gating signals, corresponding to the six possible depths or zones of focus, for delivery to a zone select circuit 206. These gating signals are in the form of six sequential control pulses having the same width.

The mode control circuit 204 may comprise a "memory" including a flip-flop circuit which will be set depending upon the mode of operation selected by the operator. The "EXPLORE/QUALITY" selector enables the operator to vary the mode of scanning between a real time of "EXPLORE" mode, wherein the beam is scanned at a first and relatively fast rate, and a "QUAL- ITY" mode wherein the ultrasonic beam is scanned at a second slower rate. Thus, after determining an area of interest in real time, a quality scan along the same plane may be initiated. The "HOLD/UNHOLD" control, which will not be further described herein, when energized stops additional information from being loaded into the storage devices which comprise the receiver-display portion of the system. The "TAKE" control, when energized, controls the operation of a camera 34 whereby photographs may be taken to provide a permanent record of the patient throughput. The "SECTIONS" control comprises an enabling switch which provides a gating signal for the control for motor 74 which produces the multiple scan mode of operation. The switches which generate the input signals to mode control 204 are located on the control panel 18.

Presuming that the "EXPLORE" mode has been selected by the operator, and the control system has been initialized in the manner known in the art, timing generator 200 will provide sequential gating signals to the zone select circuit 206 as described above. Zone selector circuit 206 also receives, as a second input, a signal generated by operation of one of a plurality of push button type controls which are also located on control panel 18; there being a separate push button for each of the six possible beam focal lengths. The zone select circuit 206 includes a counter, gates and latches which provide, in response to the two inputs, a digitally coded output signal which is commensurate with the zone selector button which has been operated. This digitally coded zone signal is applied as the control input to a zone control circuit 208 (FIG. 8A). Zone control circuit 208 may comprise a digital-to-analog function generator which provides a steady state output voltage having a magnitude commensurate with the selected zone.

Figure 10A:
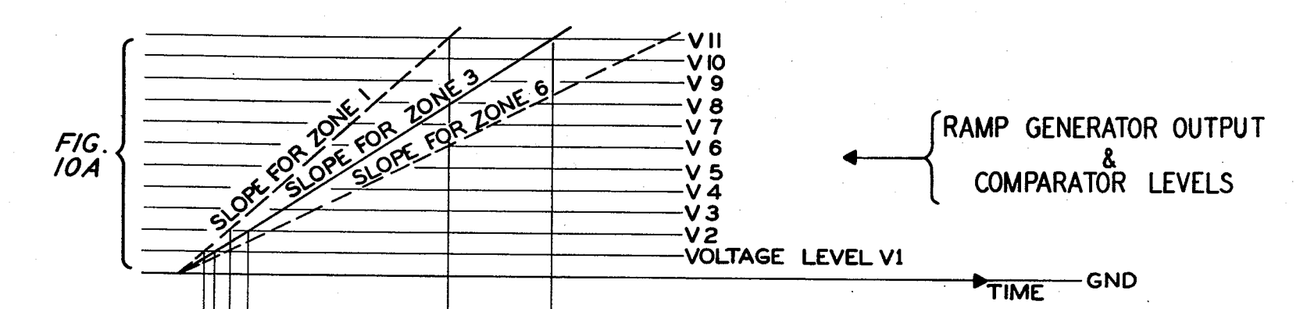
FIG. 10 is a wave form diagram related to the control circuitry of FIG. 8.

The output voltage from zone control circuit 208 is provided as the control input to ramp voltage generator 210; ramp voltage generator 210 receiving a gating signal which functions as a "start ramp" command from timing generator 200 as previously described. Ramp voltage generator 210 may comprise a conventional controllable sweep voltage generator which produces a sawtooth voltage wave form having a slope which varies in accordance with the level of the control input; i.e., the slope of the output voltage of ramp voltage generator 210 is determined by the input to the ramp voltage generator from the zone control circuit 208. Referring to FIG. 10A, three separate ramp voltage generator outputs respectively commensurate with zones or beam focal lengths Z1, Z3 and Z6 are depicted.

Figure 10B:
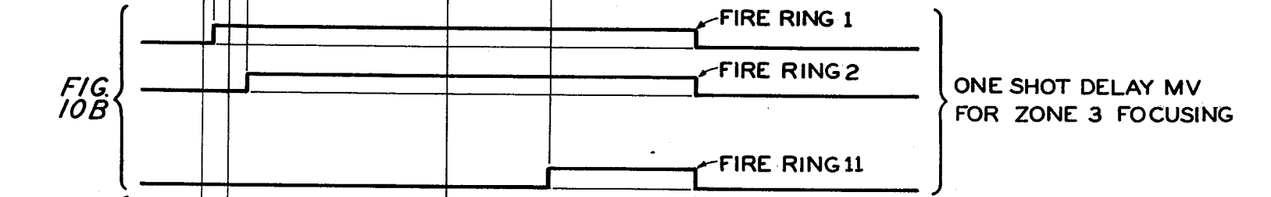

The sweep voltage outputed from ramp voltage generator 210 is delivered as the input to a plurality of identical voltage comparator circuits 212; the number of comparators being commensurate with the number of electrode rings on the transducer. Each of voltage comparators 212 is connected to receive an input bias voltage V1-Vn. The bias voltages are compared with the instantaneous magnitude of the ramp voltage from generator 210 in comparators 212. The bias voltage or comparator levels are also represented on FIG. 10A. When the ramp generator output equals the comparator bias level, the comparators will individually deliver gating signals to an associated one shot delay multivibrator 214. As indicated in FIG. 10B, the delay multivibrators have preselected periods. The time of gating of multivibrators 214 will, as should be obvious from the discussion above, be a function of the slope of the ramp voltage provided by generator 210.

Figure 10C:
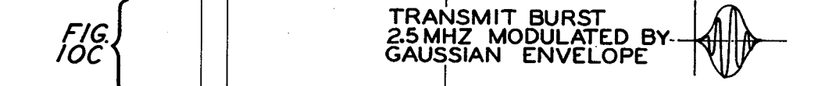
Figure 10D:
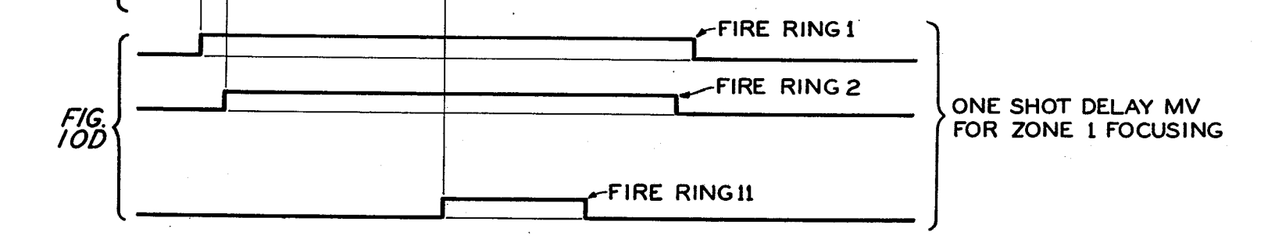

Each of delay multivibrators 214 is connected to a separate wave form generator; one of these waves form generators being indicated generally at 216 and all eleven generators 216 in the embodiment being disclosed being identical. The purpose of the wave form generators 216 is to provide a brust of electrical energy at a preselected frequency, for example 2.5MHz, and to modulate this burst of energy by a Gaussian envelope. The wave form generators 216 each include a square wave oscillator 217 which is gated into operation in response to the trailing edge of the output pulse provided by the delay multivibrator 214 to which the wave form generator is connected. Oscillator 217 provides a square wave output signal which is delivered as the input to an up-down counter 218. Counter 218, in turn, provides an input signal to a decoder 220. Decoder 220, which may for example comprise a Texas Instruments Type 7442 decoder, has four inputs connected to counter 218 and, in the example shown, six outputs which are connected, via a resistor network comprising resistors R1-R6, to the inputs to a pair of summing amplifiers 224 and 226. The summing amplifiers sum the current through the plurality of resistors to which the amplifier input is connected and provide an output signal commensurate therewith. The output signals from summing amplifiers 224 and 226 are provided as the inputs to a differential amplifier 228. The wave form generator 216 also includes a divide-by-two circuit 222 which provides a signal from decoder 220 back to counter 218 to control the direction of counting. FIG. 10C shows the wave form of the signal which appears at the output of differential amplifier 228. It may be seen that this signal has a Gaussian envelope; i.e., the output of differential amplifier 228 increases gradually to its maximum value and then decreases gradually. The shape of the envelope will be a function of the size of resistors R1-R6 and their manner of interconnection between decoder 220 and summing amlifiers 224 and 226.

It is to be observed that oscillator 217 may be variable in frequency as shown. Thus, the present invention encompasses the ability to change the frequency of drive of the transducer to select the optimum to achieve the best resolution or maximum depth of penetration of the beam. Use of a variable frequency transducer is permitted by the employment of a low Q crystal in combination with a highly damped system.

The output of the wave form generators 216, there being eleven such outputs in the embodiment being described, are delivered to individual driver amplifiers. The drivers are indicated in FIG. 8A generally at 230 and will comprise linear amplifiers with adjustable feedback resistors whereby the gain of the drivers is individually adjustable. The outputs of the drivers 230 are individually connected to the appropriate electrode rings on the transducer; the transducer being indicated on FIG. 8A at 232. From joint consideration of FIGS. 8-10, it may be seen that the selection of a particular zone through operator depression of a control button associated with zone select circuit 206, the buttons being located on panel 18, will vary the times of relative firing of the electrode rings on transducer 232 to thereby vary the depth of focus of the beam of ultrasonic energy. Side lobe suppression is enhanced by "shading" the electrodes through adjustment of the gain of the drivers; i.e., side lobes are minimized by apodization wherein different magnitude drive voltages are applied to the electrode rings.

Referring again to FIG. 8B, a further output of timing generator 200 is delivered as the control input to a stepper motor control circuit 234 which provides the control signals for stepping motor 72 (FIG. 6). The stepper motor control 234 may comprise a commercially available circuit which, in response to control signals received from timing generator 200, causes the rotor of stepping motor 72 to move through a predetermined angle. When in the EXPLORE mode, motor 72 will be advanced by one step for each sweep of ramp voltage generator 210. In the "QUALITY" mode, as a result of the control exercised over the output of timing generator 200 by mode control 204, motor 72 will be stepped with every sixth firing of transducer 232. As described above in the discussion of FIG. 7, the output shaft of stepping motor 72 is coupled to an index signal generator comprising disc 114 and sensor package 116. The output of the index signal generator is fed back as a synchronizing signal to a stepping counter 240. The motor control pulses from stepper control 234 are delivered as input signals to counter 240. Counter 240, since the number of counts required to make a complete sector scan are known, is able to provide information commensurate with the angle of deflection θ of mirror 50 and thus with the aiming of the beam of ultrasonic energy and particularly whether the beam is in the left or right half of the sector being scanned. Because of the type of drive, as discussed above in the description of FIGS. 5 and 6, it is not necessary that stepping motor 72 be reversed to accomplish the desired scanning of mirror 50 prior to initiating firing of transducer 232.

If multiple plane scanning is desired, the operator will operate the "SECTIONS" control on panel 18 thereby causing the mode control 204 to provide an enabling signal to the stepper motor control 242 for motor 74. Motor control 242 also receives, as an input, an "end of sector" signal from the stepping counter 240 associated with motor 72. Further inputs to stepper motor control 242 are a signal from a stepping counter 246 and signals generated by thumb wheel switches, located on control panel 18, which permit the operator to manually control the spacing between the multiple planes or sectors and the number of planes desired. Stepper control 242, in response to the enabling signal from mode control 204 and the initiate or "end of sector" signal from stepping counter 240, will command stepping motor 74 to advance in steps having a magnitude determined by the thumb wheel switches control input. In the same manner as with stepping motor 72, the index generator 114-116 provides a synchronizing signal which may be fed back to counter 246; counter 246 also receiving the motor control pulses from stepper control 242. Counter 246 provides a signal to control 242 indicative of the position of its rotor, and thus indicative of the angular position φ of mirror 50, which is compared in control 242 with the desired final position as established by the thumb wheel switch inputs.

Figure 8C:
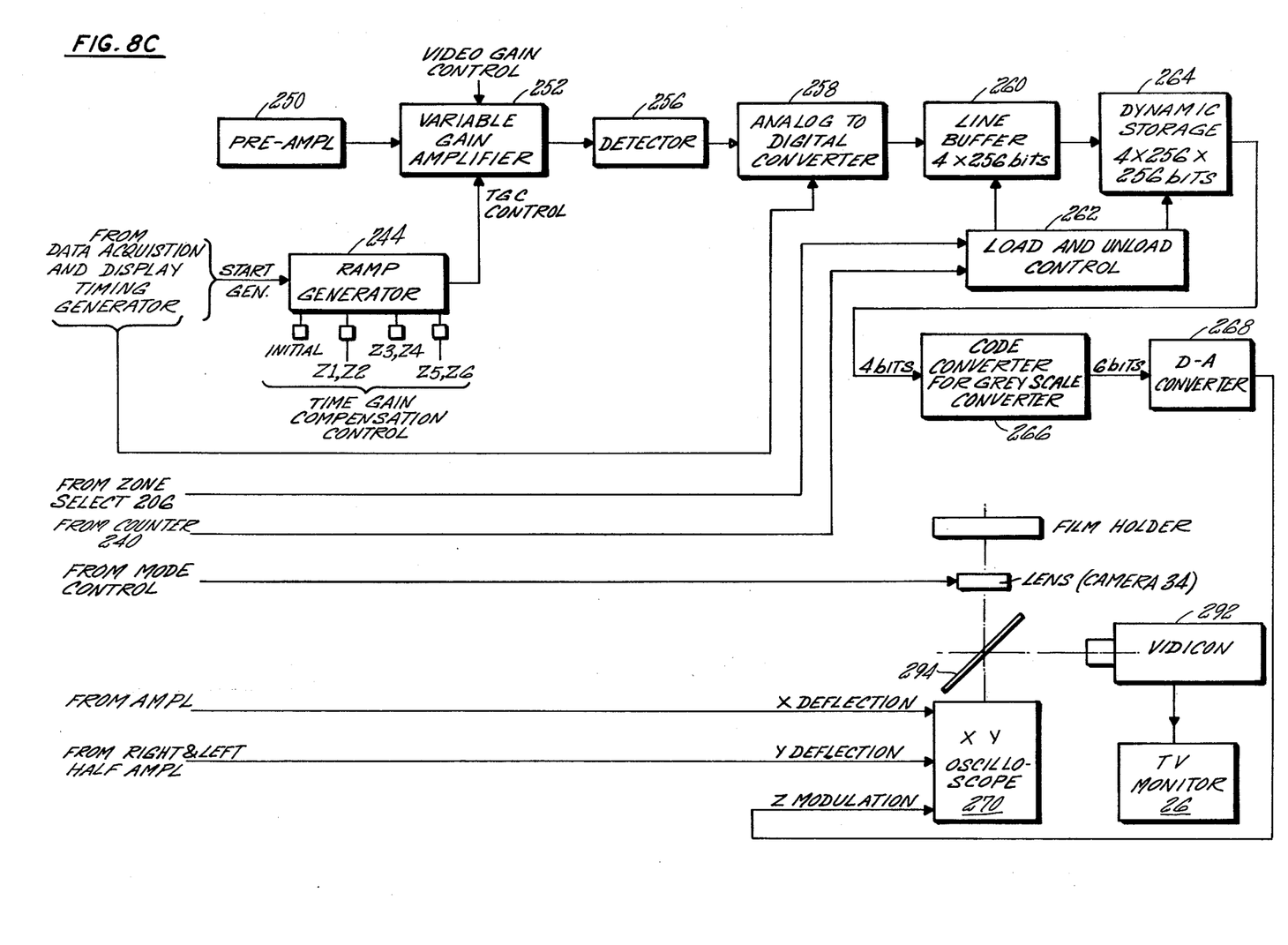
Figure 8D:
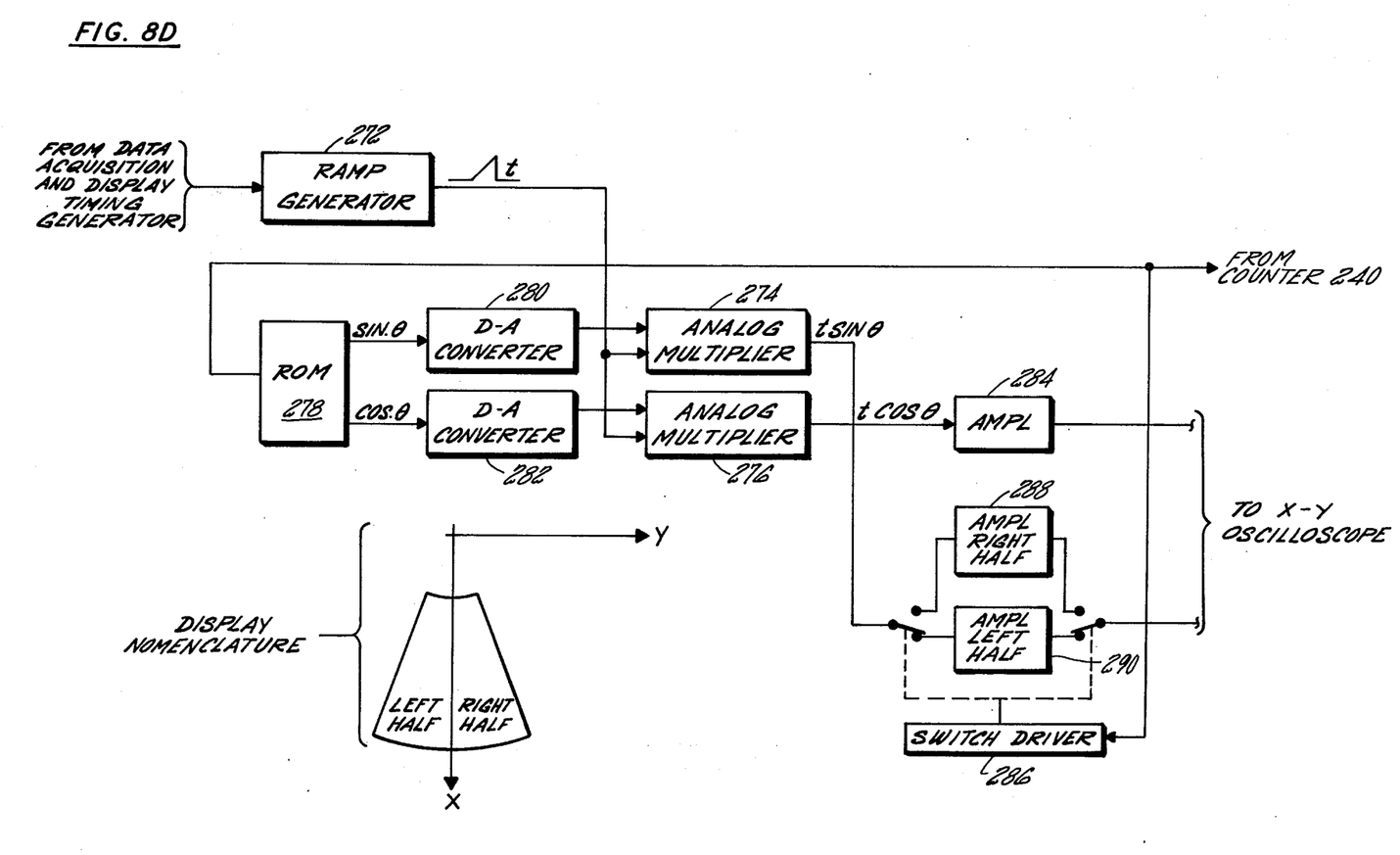
Figure 9:
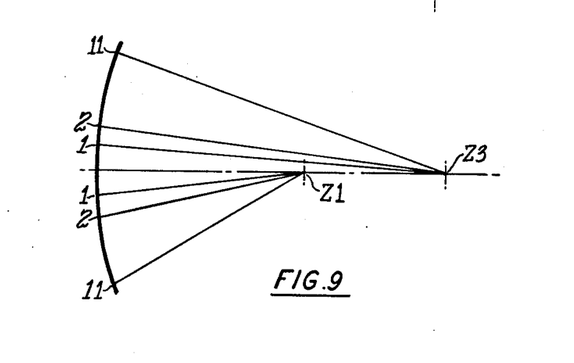
FIG. 9 is a schematic illustration of the electrical focusing of an ultrasonic transducer in accordance with the present invention.

Turning now to FIGS. 8C and 8D, all of the electrode rings on transducer 232 are connected to the input of a preamplifier 250 for initial signal enhancement. The output of preamplifier 250 is delivered as the input to a variable gain amplifier 252. Variable gain amplifier 252 is provided with a video gain control adjustment which may merely be in the form of a potentiometer. Amplifier 252 also receives a time gain control input signal from ramp voltage generator 244. Ramp voltage generator 244 comprises a controllable sweep voltage generator. The slope or slopes of the output voltage of generator 244 is selected by the operator by means of adjustment of a plurality of potentiometer inputs. Ramp voltage generator 244 receives a "start" signal from the timing generator 200, as described above, and provides an output signal which varies the gain of amplifier 252 in part as a function of the time which has elapsed since the most recent firing of the transducer 232. The "start" signal for generator 244 is delayed subsequent to the "start" of ramp voltage generator 210 (FIG. 8A) by an amount corresponding to the time required for the ultrasonic energy produced by transducer 232 to reach the patient's skin line. By adjustment of the inputs to ramp voltage generator 244, the operator may vary gain of amplifier 252 such that the amplitude of signals commensurate with received echoes passed by amplifier 252 will be a function of the distance the ultrasonic energy has traveled; i.e., those signals which have traveled the greater distance, and have thus been subject to greater attenuation, will be enhanced in comparison with echoes returning from lesser depths. The output of ramp voltage generator 244 may have as many as four different slopes in the interest of achieving the echo related signal enhancement which provides the most informative display.

The output from amplifier 252 is applied to a detector 256. Detector 256, in turn, provides an input voltage level, which varies as a function of the strength of the received echoes taking into account the gain compensation provided by amplifier 252, to an analog-to-digital converter 258. Converter 258, under the control of timing signals from timing generator 200, samples the output of detector 256 at preselected intervals which may, for example, be every one microsecond. Each time the analog-to-digital converter 258 is sampled, a digitally coded signal commensurate with the instantaneous input voltage to converter 258 is delivered to a line buffer 260.

Buffer 260 comprises 4 × 256 bits of temporary storage. Buffer 260 functions to gather the received data which is thereafter, under the control of a load and unload control circuit 260, transferred into a dynamic memory 264 which may, for example, comprise a serial shift register. The load and unload control 262 also controls outputing of data from storage circuit 264 to a grey scale code converter 266. The control inputs to the load and unload control, which may comprise merely a plurality of gating circuits, are derived from stepping counter 240 and zone control circuit 206. The input to load and unload control circuit 262 derived from counter 240 determines the address in buffer 260 where the sampled data is stored. The input to load and unload control 262 provided by the zone select circuit 206 controls the loading and unloading of buffer 260 and memory 264. Stored data is transferred from buffer 260 into memory 264 subsequent to receipt of all echoes associated with a single "firing" of transducer 232 in the "EXPLORE" mode and after every sixth burst in the "QUALITY" mode.

To further discuss the difference between the "EXPLORE" and "QUALITY" modes of operation, when operating in the "QUALITY" mode the input to the zone select circuit 206 provided by mode control circuit 204 in effect causes the serial operation of the switches associated with the push button controls of the zone select circuit. Thus, when in the "QUALITY" mode, the zone select circuit 206 will serially provide outputs to the zone control circuit 208 commensurate with the six possible focal lengths of the beam of ultrasonic energy. As noted above, zone select circuit 206 also provides a control signal, indicative that the "QUALITY" mode is desired, to the load and unload control 262. This "QUALITY" mode input signal results in the load and unload control providing a signal which enables the input to line buffer 260 only at times commensurate with the receipt of echoes from the zone which has been selected by the automatic sequencing. Thus, before the mirror 50 is stepped to a next position, in the disclosed embodiment the transducer 232 will be "fired" six times and for each of these bursts of ultrasonic energy the timing of the application of the drive signals to the annular electrodes on the transducer will be varied so that each burst of ultrasonic energy will be focused at a different depth. Echoes received from the zone commensurate with the instantaneous beam focal length, and only these echoes, will be loaded into line buffer 260 and when the signals corresponding to the echoes from the six zones have been loaded into line buffer 260, the mirror 50 will be stepped to its next position and the stored information transferred from line buffer 260 into memory 264. Accordingly, it may be seen that the present invention has the ability to perform a fast scan, so as to provide real time information, with a beam of ultrasonic energy which has a fixed but operator selected focal length. In this "EXPLORE" mode, movements such as the pulsating of blood vessels may be observed on the TV monitor 26. When switched to the "QUALITY" mode, the scanning of the beam is slowed down to enable the focal length of the beam to be automatically varied with the transducer being "fired" a number of times commensurate with the available zones of focus before being moved to the next position in the scanning plane.

Since photographic film is nonlinear, and it is desirable to produce equal steps in shading for the various echo levels received, the grey scale code converter 266 is utilized. Converter 266 generates a transfer function whereby the information outputed from storage circuit 264, which is in the form of four bits, will be converted into six bits of information commensurate with sixty-four discrete levels of grey. The digital output information from converter 266 is applied to a digital-to-analog converter 268. The output of converter 268 functions as the modulation input signal to an oscilloscope 270 located within equipment cabinet 30.

Referring to FIG. 8D, the circuitry for synchronizing the display with the scanning of the ultrasonic beam is shown. The display control circuitry includes ramp voltage generator 272 which receives "start ramp" control pulses from timing generator 200. The sweep voltage produced by generator 272 is applied as first inputs to a pair of analog multipliers 274 and 276. The display control circuitry also includes a programmed read only memory 278 which receives signals provided by the counter 240 which is associated with the sector scan drive motor 72. In response to the output signal provided by counter 240, which is indicative of the angular relationship of the mirror to its centered position, memory 278 will output a pair of digital signals respectively commensurate with the sine and cosine of the instantaneous mirror angle $\theta$. These sine and cosine signals are converted, in respected digital-to-analog converters 280 and 282, to analog signals and applied as second inputs to respective multipliers 274 and 276. Accordingly, multiplier 274 will provide an output signal having a magnitude which varies as a product of the sine of the angle $\theta$ of mirror 50 relative to its undeflected position and the time which has elapsed since the beginning of the scan. Similarly, multiplier 276 will also provide an output signal corresponding to the product of the mirror angle O and the elapsed time. The output of multiplier 276 is applied to an amplifier 284 and the output of this amplifier controls the "X" deflection of oscilloscope 270. The output of multiplier 274 is, depending on the status of a switch driver circuit 286, applied either to a "right half" amplifier 288 or a "left half" amplifier 290. Switch driver 286 is controlled by the output of counter 240 and insures that the appropriate amplifier output will be utilized to obtain the requisite "Y" deflection signal for oscilloscope 270 as a function of the position of mirror 50. FIG. 8D indicates the display nomenclature and shows why it is necessary to employ a switch driver circuit 286 and amplifiers 288 and 290 in order to form, on the CRT of oscilloscope 270, an accurate representation of the scanning plane. The output signal from either of amplifiers 288 or 290 is applied as the "Y" axis deflection control signal for oscilloscope 270.

Referring again to FIG. 8C, a TV camera 292 is located within equipment cabinet 30 and, via a splitter plate 294, observes the image formed on the CRT of oscilloscope 270. The output of camera 292 is delivered to TV monitor 26 (FIG. 1).

The still camera 34 also views, via splitter plate 294, the display on oscilloscope 270. By depressing the "take" button associated with mode control circuit 204, the operator can cause the shutter of the camera 34 to be tripped whereby a photograph may be taken whenever the operator observes something of interest on the TV monitor thus preserving a permanent record for further study. The apparatus will also include an automatic film advance which is energized when the camera shutter is operated.

While preferred embodiments have been shown and described, various modifications and substitutions may be made thereto without departing from the spirit and scope of the invention.

Accordingly, it is to be understood that the present invention has been described by way of illustration and not limitation.

What is claimed is:

1. A method of non-destructive and non-invasive testing comprising the steps of:
   energizing an ultrasound transducer in such a manner as to cause an intermittent beam of ultrasonic energy having a preselected focal length to be generated;
   directing the generated ultrasonic energy beam to an object to be tested, the focal point of the beam being within the object;
   scanning the beam at a first rate of speed so as to move the beam focus point along a line whereby a sector of the object is tested;
   receiving echoes from the boundries of regions within the object which are characterized by different impedances to the passage of ultrasonic energy;
   displaying the received echoes;
   rescanning the beam along the line at a second rate of speed which is slower than said first rate of speed when an area of interest within the object is observed from the displayed echoes; and
   refocusing the beam to a plurality of different focal lengths during the rescanning thereof.

2. The method of claim 1 wherein the step of rescanning the beam comprises:
sweeping the beam along the line in stepwise fashion.

3. The method of claim 2 wherein the step of refocusing comprises:
refocusing between the steps comprising the second rate of scanning.

4. The method of claim 1 wherein the step of directing the beam of ultrasonic energy to the object to be tested comprises:
transmitting the beam through a liquid medium; and
coupling the liquid medium to the object to be tested by bringing a flexible member which in part confines the liquid medium into contact with the surface of the object.

5. The method of claim 4 wherein the steps of scanning and rescanning comprise:
establishing a nonlinear path between the transducer and the object to be tested;
inserting an acoustical mirror in the nonlinear path in a position to be impinged upon by the beam; and
varying the angular position of the mirror.

6. The method of claim 1 wherein the steps of scanning and rescanning comprise:
establishing a nonlinear path between the transducer and the object to be tested;
inserting an acoustical mirror in the nonlinear path in a position to be impinged upon the beam; and
varying the angular position of the mirror.

7. The method of claim 1 further comprising:
varying the frequency of the generated ultrasonic energy with each refocusing of the beam to optimize the testing procedure.

8. The method of claim 5 further comprising the step of:
varying the frequency of the generated ultrasonic energy with each refocusing of the beam to optimize the testing procedure.

9. The method of claim 6 wherein the step of varying the angular position of the mirror while scanning the beam at a first rate comprises:
rotating the mirror in a first direction about an axis in stepwise fashion whereby the focal point of the beam transcribes a line within the object.

10. The method of claim 9 wherein the step of directing the beam of ultrasonic energy to the object to be tested comprises:
transmitting the beam through a liquid medium; and
coupling the liquid medium to the object to be tested by bringing a flexible member which in part confines the liquid medium into contact with the surface of the object.

11. The method of claim 10 further comprising the step of:
rotating the mirror in stepwise fashion in a second direction generally transverse to said first direction whereby the transcribed line will be shifted and multiple planes within the object scanned.

12. The method of claim 11 wherein the step of rescanning the beam comprises:
sweeping the beam along each transcribed line in stepwise fashion.

13. The method of claim 12 wherein the step of refocusing comprises:
refocusing between the steps comprising the second rate of scanning.

14. The method of claim 13 further comprising the step of:
varying the frequency of the generated ultrasonic energy to optimize the testing procedure.

15. Apparatus for use in the non-destructive and non-invasive testing of objects comprising:
transducer means, said transducer means including a piezoelectric crystal having disposed on at least one surface thereof an array of coaxial annular electrodes, said transducer means generating a focused beam of ultrasonic energy in response to the application of electrical signals to said electrodes;
housing means, said housing means supporting said transducer means and having an exit opening for the beam of ultrasonic energy generated by said transducer means, said housing means defining a nonlinear path between said transducer means and said exit opening;
first flexible means for coupling said housing means exit opening to a test object;
a liquid disposed in said housing means, said liquid defining the transmission path for the beam of ultrasonic energy from said transducer means to said first flexible member;
an acoustical mirror disposed in said housing means between said transducer means and said housing means exit opening, said acoustical mirror redirecting the beam of ultrasonic energy generated by transducer means to said exit opening;
receiver means, said receiver means being electrically connected to said transducer means and being responsive to electrical signals produced by said crystal upon interception by said transducer means of ultrasonic energy returned from within the body by reflection from boundaries between regions characterized by different ultrasound transmission characteristics, said receiver means processing said electrical signals to provide an information containing output signal;
means connected to said receiver means and responsive to the output of said receiver means for providing a reviewable record of a region of the object being tested;
driving signal generating means; and
means for coupling driving signals provided by said driving signal generating means to said transducer means annular electrodes.

16. The apparatus of claim 15 wherein said transducer means crystal is shaped to have a natural focal length.

17. The apparatus of claim 15 wherein said driving signal generating means comprises:
a plurality of signal generators, said signal generators being commensurate in number with the number of annular electrodes on said transducer means crystal.

18. The apparatus of claim 17 wherein said signal generators each comprise:
means for generating a signal having a predetermined wave form; and
means for selectively varying the time of generation of said signal of predetermined wave form whereby the relative time of application of signals to said annular electrodes may be varied to thereby vary the focal length of the beam of ultrasonic energy.

19. The apparatus of claim 18 wherein said transducer means crystal is shaped to have a natural focal length.

20. The apparatus of claim 19 wherein said beam focal length is varied about the natural focal length thereof.

21. The apparatus of claim 18 wherein said means for generating a signal having a predetermined wave form each comprises:
   an oscillator;
   modulator means for modulating the output of said oscillator to produce an envelope having a wave form which increases gradually to a maximum value and thereafter decreases gradually.

22. The apparatus of claim 21 wherein said means for selectively varying the time of generation of said signal of predetermined wave form each comprises:
   gating signal generating means, said gating signal generating means providing a gating signal for controlling the provision of a signal by said oscillator; and
   means for generating a control signal for said gating signal generating means, said gating signal generating means control signal being manually variable to vary the time of generation of said gating signals.

23. The apparatus of claim 22 wherein the output frequency of each of said oscillators may be varied.

24. The apparatus of claim 15 further comprising:
   means for moving said acoustical mirror to cause said beam of ultrasonic energy to be scanned along a line.

25. The apparatus of claim 24 wherein said means for moving said acoustical mirror comprises:
   first means for tilting said mirror to cause the beam of ultrasonic energy to scan in a first direction along a line; and
   second means for tilting said mirror in a direction generally transverse to said first direction to cause said scanning lines to be displaced.

26. The apparatus of claim 18 further comprising:
   means for moving said acoustical mirror to cause said beam of ultrasonic energy to be scanned along a line.

27. The apparatus of claim 26 wherein said means for moving said acoustical mirror comprises:
   first means for tilting said mirror to cause the beam of ultrasonic energy to scan in a first direction along a line; and
   second means for tilting said mirror in a direction generally transverse to said first direction to cause said scanning lines to be displaced.

28. The apparatus of claim 27 wherein said means for generating a signal having a predetermined wave form each comprise:
   an oscillator;
   modulator means for modulating the output of said oscillator to produce an envelope having a wave form which increases gradually to a maximum value and thereafter decreases gradually.

29. The apparatus of claim 28 wherein said transducer means crystal is shaped to have a natural focal length.

30. The apparatus of claim 29 wherein said beam focal length is varied about the natural focal length thereof.

31. The method of claim 1 further comprising the step of:
   shifting the scanning lines in a transverse direction in stepwise fashion to permit the testing of multiple planes within the object being tested.

32. The method of claim 31 further comprising the step of:
   varying the frequency of the generated ultrasonic energy to optimize the testing procedure.

33. Apparatus for use in the non-destructive and non-invasive testing of objects comprising:
   transducer means, said transducer means including a piezoelectric crystal and generating a beam of ultrasonic energy in response to electrical stimulation of said crystal;
   means for supporting said transducer means whereby the generated ultrasonic energy will be coupled to a body to be tested;
   receiver means, said receiver means being electrically connected to said transducer means and being responsive to electrical signals produced by said transducer means upon interception by said transducer means of ultrasonic energy returned from within the body by reflection from boundaries between regions characterized by different ultrasound transmission characteristics, said receiver means processing said electrical signals to provide an information containing output signal;
   variable frequency oscillator means for providing periodic output signals in response to gating signals;
   modulator means responsive to the output signals of said oscillator means for producing amplitude modulated signals which increase gradually from a minimum to a maximum level and thereafter decrease gradually to the minimum level;
   means for coupling said amplitude modulated signals to said transducer means to actively drive said transducer means;
   means for generating gating control signals for said oscillator means; and
   means for varying the focus of said transducer means.

34. The apparatus of claim 33 wherein said modulator means provides a plurality of amplitude modulated output signals and said transducer means crystal is provided with an annular array of electrodes, individual of said amplitude modulated signals being applied to individual of said electrodes of said array by said coupling means.

35. The apparatus of claim 34 wherein said focus varying means comprises:
   means for selectively adjusting the relative times of generation of said amplitude modulated signals to electrically vary the focus of said transducer means.

36. The apparatus of claim 15 wherein the outer one of said transducer means annular electrodes is segmented, the width of said segmented electrodes being less than 10 wavelengths of the frequency of the generated ultrasonic energy.

* * * * *